United States Patent [19]

Schneider

[11] Patent Number: 5,073,170
[45] Date of Patent: Dec. 17, 1991

[54] DRAINAGE TUBE RETENTION DEVICE

[75] Inventor: Barry L. Schneider, Deerfield, Ill.

[73] Assignee: Hollister Incorporated, Libertyville, Ill.

[21] Appl. No.: 676,564

[22] Filed: Apr. 28, 1991

Related U.S. Application Data

[63] Continuation of Ser. No. 564,571, Aug. 9, 1990, abandoned.

[51] Int. Cl.$^5$ ................................................ A61M 5/32
[52] U.S. Cl. ................................ 604/180; 128/DIG. 26
[58] Field of Search ............... 604/180, 179, 178, 174; 128/DIG. 26

[56] References Cited

U.S. PATENT DOCUMENTS

| | | | |
|---|---|---|---|
| 2,900,696 | 8/1959 | Bacon | 24/206 |
| 2,979,794 | 4/1961 | Bartolo | 24/17 |
| 3,009,220 | 11/1961 | Fein | 24/16 |
| 3,049,771 | 8/1962 | Litwin et al. | 24/16 |
| 3,074,675 | 1/1963 | Brown | 248/68 |
| 3,214,808 | 11/1965 | Litwin | 24/16 |
| 3,653,096 | 4/1972 | Fernberg | 24/16 PB |
| 3,761,999 | 10/1973 | Morgan | 24/16 PB |
| 3,855,669 | 12/1974 | Meyer | 24/16 PB |
| 3,900,923 | 8/1975 | Thomas | 24/16 PB |
| 3,942,750 | 3/1976 | Noorily | 248/74 PB |
| 4,008,512 | 2/1977 | Prodel | 24/16 PB |
| 4,079,485 | 3/1978 | Collier et al. | 24/16 PB |
| 4,236,280 | 12/1980 | Kreiseder | 24/16 PB |
| 4,392,857 | 7/1983 | Beran | 604/179 |
| 4,585,443 | 4/1986 | Kaufman | 128/DIG. 26 |
| 4,699,616 | 10/1987 | Nowak et al. | 604/180 |
| 4,874,380 | 10/1989 | Hesketh | 604/180 |

*Primary Examiner*—John D. Yasko
*Attorney, Agent, or Firm*—Tilton Fallon Lungmus

[57] ABSTRACT

A device for releasably retaining a drainage tube in place at its site of exit from a patient's body. The device includes a resilient, adhesive pad for attachment to a patient's skin and a flexible plastic retainer secured to the upper surface of the pad, the retainer including a mounting plate having an enlarged recess extending inwardly from its periphery and a flexible strap formed integrally with the plate and extending outwardly through the recess and beyond the periphery of the plate. The strap is Y-shaped in configuration with its diverging arms secured to the plate at points disposed on opposite sides of an opening formed in an upstanding wall of the plate. The tongue portion of the Y-shaped strap may be reversely turned and inserted through that opening from the direction of the spaced arms. A latching member on the opposite side of the wall has depending teeth which are engagable with teeth on the reversely-turned strap to secure the strap about a drainage tube.

14 Claims, 3 Drawing Sheets

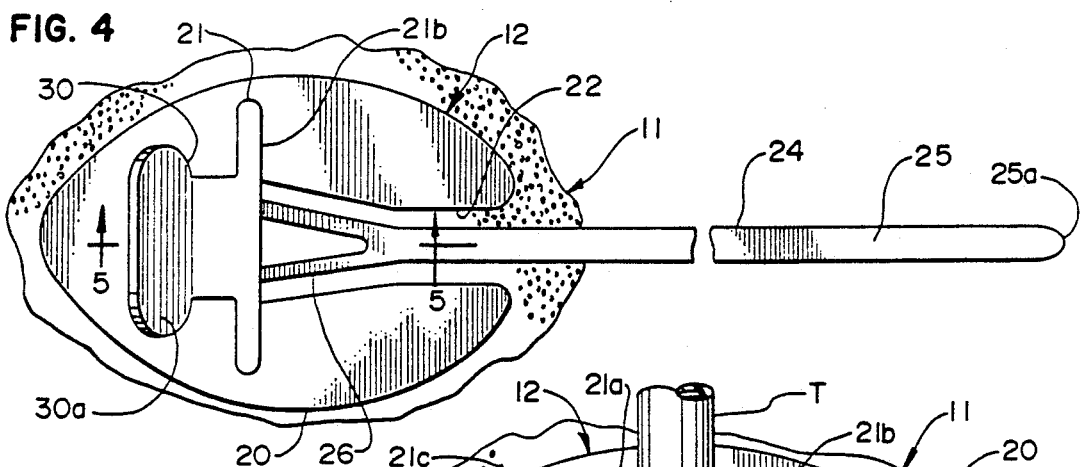
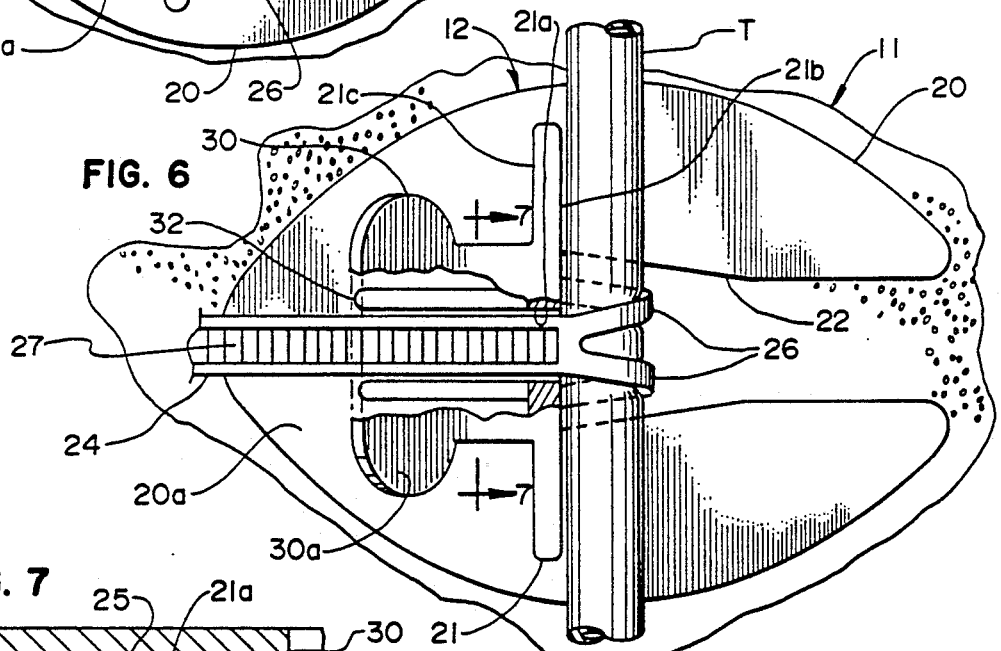
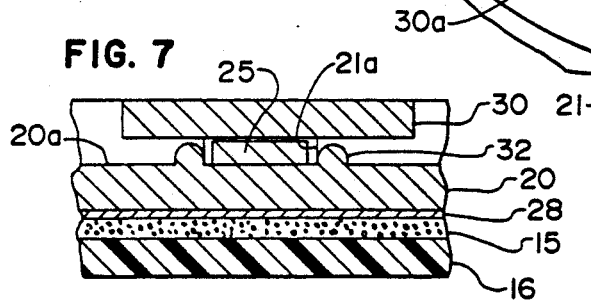
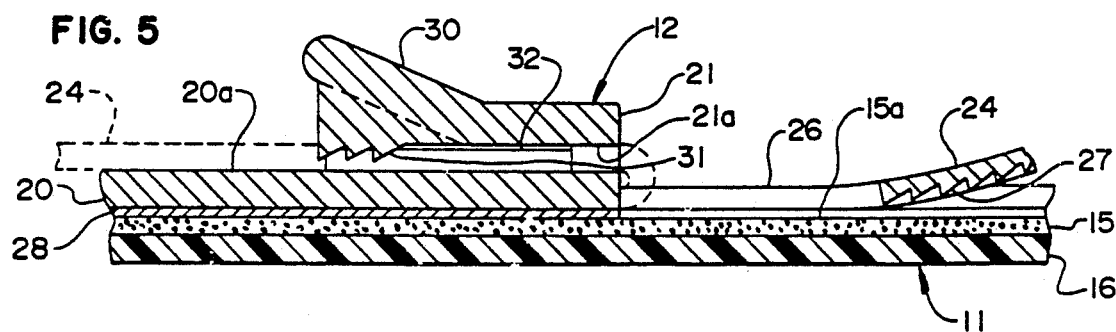

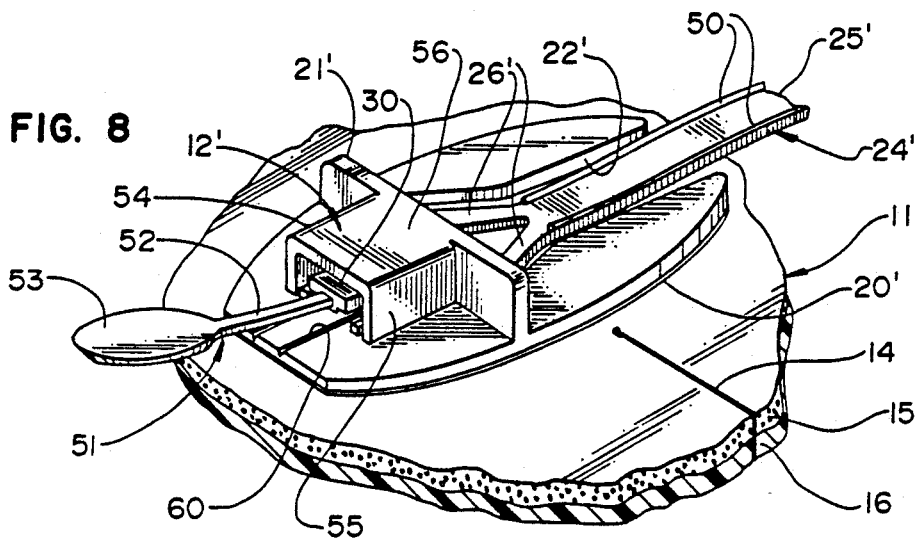
FIG. 8
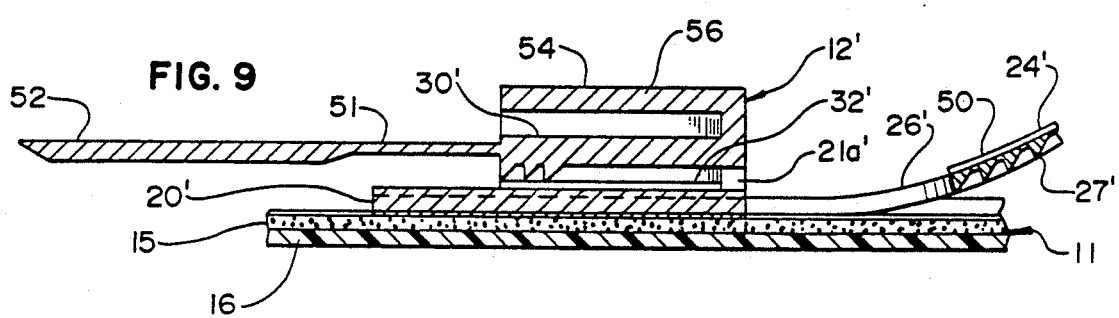
FIG. 9
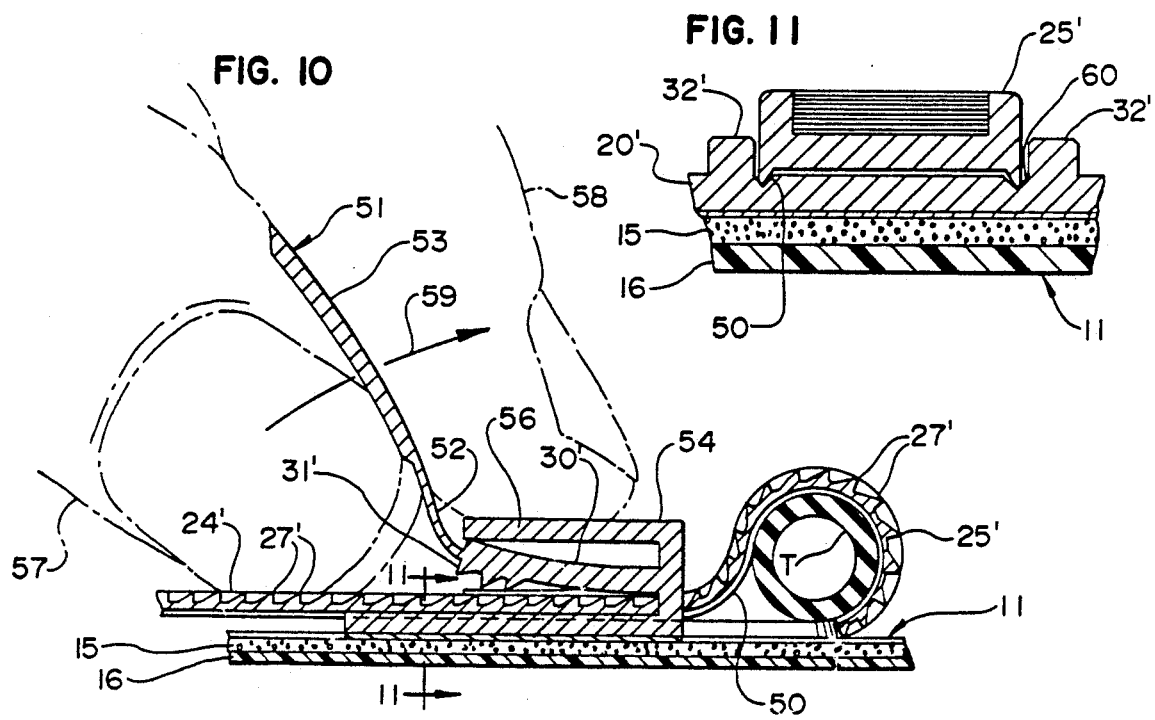
FIG. 10
FIG. 11

DRAINAGE TUBE RETENTION DEVICE

RELATED APPLICATION

This application is a continuation of application Ser. No. 564,571, field Aug. 9, 1990 now abandoned.

BACKGROUND AND SUMMARY

While it is apparent that post-surgical drainage tubes or catheters should be securely attached so that they are not inadvertently dislodged or withdrawn by patients or hospital staff, and while it is well recognized that a wound or incision area, including surrounding skin surfaces, should be protected against irritating and excoriating effects of fluid contact, prior devices have generally fallen short of achieving such objectives, at least without introducing additional problems that offset their advantages. Thus, to help immobilize an indwelling catheter, it is a common practice to suture the catheter to a retention device and also suture the retention device to a patient's skin. The former does not always insure against catheter movement and the latter may result in irritation, infection, and considerable patient discomfort over the typical period of catheter placement (usually five to seven days).

Co-owned U.S. Pat. No. 4,699,616 discloses a catheter retention device which does reduce if not eliminate many of the problems associated with prior devices. It may be securely attached to a patient without sutures and without threading the catheter or drainage tube through an opening in the device, and it may be easily manipulated to secure the catheter against inadvertent extraction. The device also includes a pad that provides a continuous or uninterrupted barrier zone about the exit site for the catheter, thereby protecting the surrounding skin from the excoriating effects caused by contact with exudate.

One aspect of the patented construction that may be considered advantageous under some circumstances but disadvantageous under others is that the clamping jaws of the retainer extend a substantial distance outwardly away from the patient's skin and hold the drainage tube in a direction extending perpendicular to the skin surface. Both the device and the tube therefore extend a substantial distance outwardly from that surface. In addition, the clamping jaws operate effectively with drainage tubes in the standard size ranges but may not be equally as effective with tubes of smaller or larger sizes.

Accordingly, the present invention is directed to a catheter or drainage tube retention device that may be easily manipulated to securely grip tubes of a smaller range of sizes, such as those having outside diameters within the range of about 1 to 7 millimeters, while also being effective in holding tubes of larger size (e.g., 7 to 14 millimeters). In addition, the device is relatively flat, projecting only minimal distance from a patient's skin. Although the tube is held in a direction parallel to the skin surface rather than perpendicular to that surface, kinking is nevertheless avoided because the relationship of parts allows a portion of the tube between the exit point and the retaining means to assume a gentle curve or change in direction.

Briefly stated, the drainage tube retention device of this invention includes a flexible adhesive pad for attachment to the skin, the pad having an adhesive layer that preferably takes the form of a moisture-absorbing skin barrier material having both wet and dry tack, and tube retaining means formed integrally of flexible plastic material adhesively secured to the upper surface of the pad. The tube retaining means includes a mounting plate having a generally planar top surface and an integral wall or rib projecting upwardly from that surface. An opening in the wall extends in a direction parallel with the plane of the plate, and a recess formed in the plate extends from one side of the wall immediately adjacent the opening to the outer periphery of the plate. A flexible strap formed integrally with the plate extends outwardly through the recess to a point substantially beyond the plate's outer periphery. The strap is Y-shaped in configuration with the arms of the Y joined to the plate at points on opposite sides of the opening in the wall. In use of the device, the elongated stem or tongue of the strap is turned in a reverse direction and inserted through the opening. Because of the Y-shaped configuration of the strap and the construction of the associated parts of the device, the strap may be advanced through the opening until the loop formed by the strap is diminished almost if not completely to zero diameter. Thus, the strap may be looped about a drainage tube or catheter extending alongside the wall of the device and, regardless of the cross sectional dimensions of the catheter within the full range of standard sizes commonly used for drainage purposes, the catheter will be securely immobilized against longitudinal sliding movement by the tube retaining device.

Unlike many other tube retaining devices used in the past, this device does not require the tube to be threaded through an opening provided by the gripping means. Instead, the strap is simply wrapped about a tube that exits from the body through an opening in the sealant pad and extends along the wall of the tube retaining means secured to that pad.

Latching means on the opposite side of the wall adjacent the opening engages the protruding end of the strap and prevents unintended retrograde movement of the strap. Such latching means takes the form of a flexible latching member that projects from the wall above the top surface of the plate. The underside of that member and the upwardly exposed surface of the protruding end of the strap are provided with interengaging teeth that lock the strap against retrograde movement unless the latching member is intentionally lifted while the strap is simultaneously urged in a reverse direction. The surface of the plate below the latching member is imperforate and serves as a smooth, non-yielding support that prevents movement of the strap away from the latching member in response to the downward force exerted by that member. Guide shoulders along the top surface of the plate help guide movement of the end of the strap out of the opening in the transverse wall and into position for latching engagement with the flexible latching member.

Other features, objects, and advantages of the invention will become apparent from the specification and drawings.

DRAWINGS

FIG. 4 is a fragmentary top plan view of the device showing the molded tube retaining means therefor.

FIG. 5 is an enlarged vertical sectional view taken along line 5—5 of FIG. 4.

FIG. 6 is an enlarged plan view similar to FIG. 4 but depicting the parts in use in the retention of a drainage tube, with certain portions of the drawing broken away to illustrate structural features of particular interest.

FIG. 7 is an enlarged fragmentary cross sectional view taken along line 7—7 of FIG. 6.

FIG. 8 is a fragmentary perspective view of a drainage tube attachment device constituting a second embodiment of the invention.

FIG. 9 is an enlarged vertical sectional view taken along line 9—9 of FIG. 8.

FIG. 10 is an enlarged sectional view similar to FIG. 9 but showing the relationship of parts when the attachment device is being unlatched.

FIG. 11 is a still further enlarged vertical cross sectional view taken along line 11—11 of FIG. 10.

DETAILED DESCRIPTION OF PREFERRED EMBODIMENT

Figure 1:
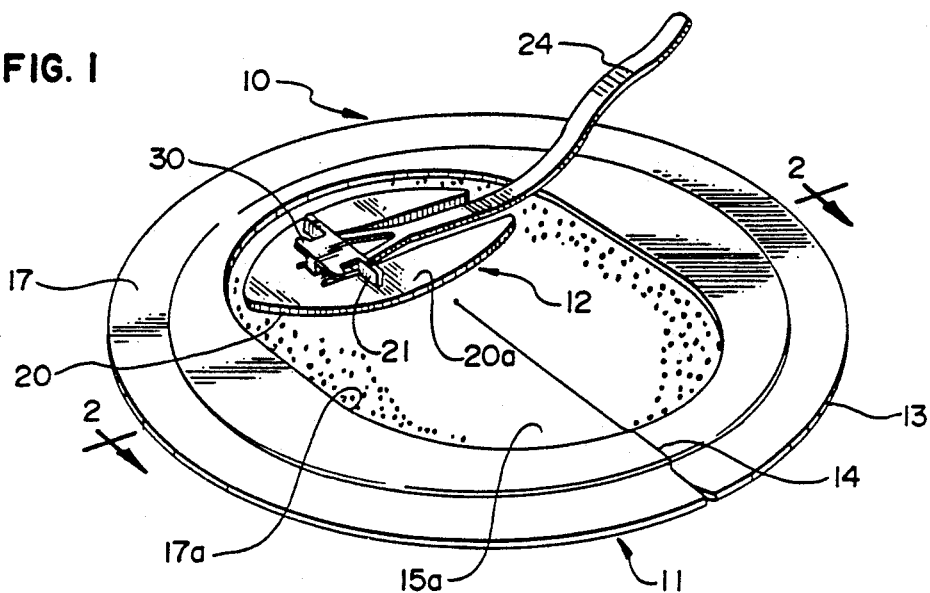
FIG. 1 is a perspective view of a drainage tube attachment device embodying the present invention.
Figure 2:
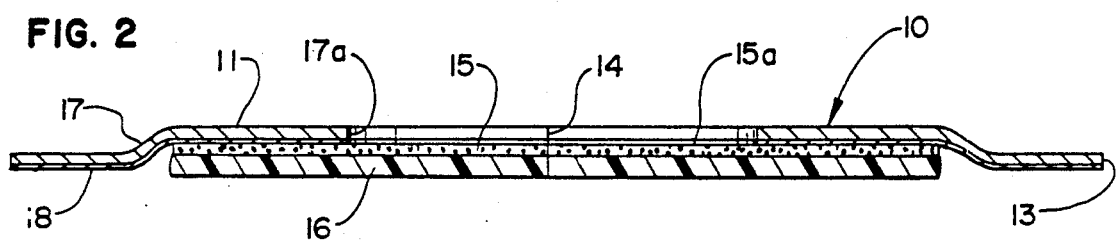
FIG. 2 is an enlarged and somewhat schematic cross sectional view taken along line 2—2 of FIG. 1.
Figure 3:
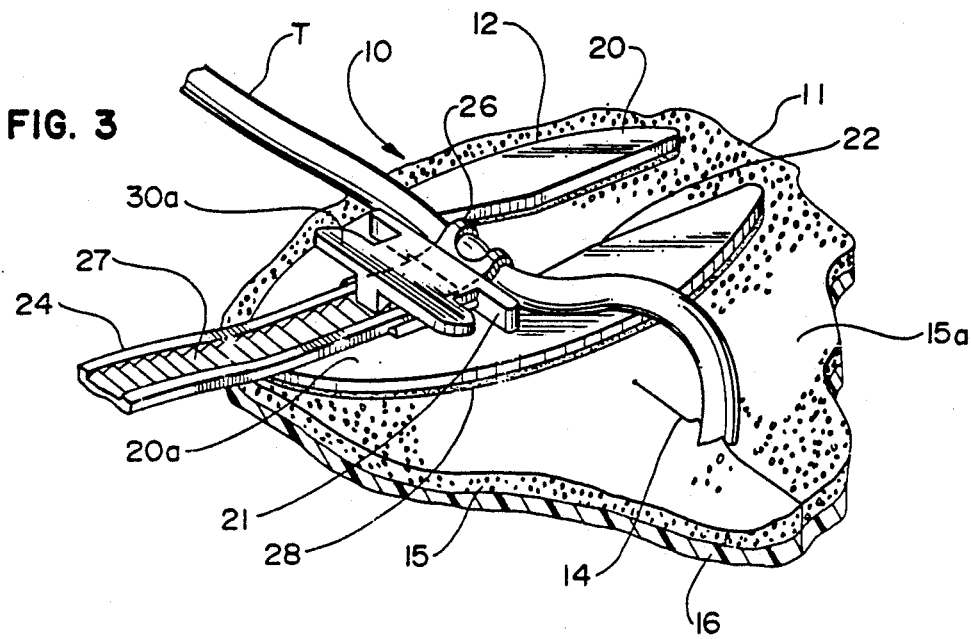
FIG. 3 is an enlarged fragmentary view showing a portion of the device as it would appear in use in securing a drainage tube in position.

Referring to FIGS. 1-7 of the drawings, numeral 10 generally designates a drainage tube retention device composed of a flexible barrier pad 11 and tube retaining means in the form of a molded plastic tube retainer 12. The illustrated pad is planar and has a generally circular periphery 13 although other shapes may be used. A radial entry slit 14 extends transversely with respect to the retainer, terminating in close proximity to that retainer. Preferably, the retainer 12 is offset from the center of the pad and the slit 14 has a length exceeding the pad's radial dimension. Such a relationship allows the pad to be centered over a catheter exit opening with the catheter then extending generally upwardly through the center of the pad as indicated in FIG. 3.

The materials and construction of the pad may be varied considerably as long as the thin, planar pad is flexible and generally conformable with body contours, is sufficiently deformable to permit the edges of slit 14 to be brought into tight contact with each other, and is provided along its underside with a suitable pressure-sensitive adhesive material that not only immobilizes the pad on the patient's skin but also performs a sealing function in protecting the skin against fluid contact. A particularly advantageous construction is depicted in the drawings where pad 11 is shown to be composed of an upper layer 15 of resilient, flexible, fine-celled thermoplastic foam, such as a polyolefin or polyurethane foam, a lower layer 16 of soft, deformable skin barrier material having both wet and dry tack (such as karaya or a barrier composition of the type designated as "Hollihesive" by Hollister Incorporated, Libertyville, Illinois), and a surrounding layer 17 of a suitable microporous material such as the gas-permeable but liquid-impermeable non-woven microporous material disclosed in U.S. Pat. No. 4,213,458. The underside of the surrounding microporous layer 17 is coated with any suitable medical-grade pressure-sensitive adhesive 18 such as the hypo-allergenic acrylic adhesive commonly used in medical applications. The pressure-sensitive adhesive layer 18 of the microporous border layer 17, and the tacky undersurface of barrier layer 16, may be covered by one or more removable silicone-coated release sheets (not shown). As illustrated in FIGS. 1 and 2, the microporous layer 17 covers only a border area of the foam layer's upper surface 15a, and has an enlarged opening 17a that exposes the major central area of upper surface 15a.

The tube retainer 12 is a unitary part molded from polypropylene, Nylon, or other flexible thermoplastic material and includes a generally planar plate 20 of generally elliptical outline with a transverse wall 21 projecting upwardly from the top surface 20a of the plate. As shown in the drawings, upstanding wall 21 is parallel with the slit 14 and slightly offset from the vertical plane of that slit. An opening 21a extends through the wall in a direction normal to the vertical plane of slit 14, and a horizontal recess 22 in the plate 20 extends from one side 21b of the wall immediately adjacent opening 21a to the outer peripheral edge of the plate.

The retainer also includes a flexible strap 24 formed integrally with the plate 20 and extending outwardly from wall 21 through recess 22 to a point well beyond the periphery of the plate. The strap is generally Y-shaped in configuration and includes an elongated central tongue portion 25 and a pair of diverging arm portions 26. The arm portions 26 have their distal ends merging with the tongue portion 25 and their proximal ends joined to the plate 20 at points lateral to the opening 21a in wall 21 to define a generally triangular space between the arm portions. The tongue 25 is of substantially uniform width throughout its full length, such width being slightly less than that of opening 21a. The free end 25a of the tongue is rounded or tapered as shown in FIG. 4 to facilitate insertion through opening 21a, and the underside of the tongue is provided with a longitudinal series of transversely extending teeth 27.

The bottom of plate 20 is coated with a layer of adhesive 28 for securely affixing the plate to the upper surface 15a of foam layer 15. While adhesive attachment is preferred, it is to be understood that any other means for securely and permanently affixing the plate to the upper surface of the pad may be provided.

The tube retainer also includes a latching member 30 that extends from side 21c of the wall opposite from side 21b. The underside of the latching member is provided with at least one tooth 31, and preferably a plurality of such teeth, engagable with the teeth 27 of the strap when the strap is turned upwardly and rearwardly upon itself and its free end 25a is inserted through opening 21a from the direction of arm portions 26. The teeth are shaped to permit advancement of the strap but block retrograde movement unless the flexible member 30 is lifted so that its teeth are disengaged from those of the strap. As shown most clearly in FIGS. 5 and 7, the surface 20a of plate 20 directly beneath latching member 30 is smooth and imperforate, thereby providing a firm support surface for the tongue 25 of the strap in the zone of engagement with latching member 30. Since such portion of the plate is imperforate, the strap cannot flex downwardly out of engagement with teeth 31 of the latching member. A pair of parallel shoulders 32 may be provided along surface 20a to guide movement of the strap and insure proper positioning of the strap beneath latching member 30.

In use of the device, a cross-slit may be manually formed in the pad at a point along slit 14 where the nurse or doctor determines that a drainage tube T should extend through the pad. If the tube is of small outside diameter (e.g. one millimeter or 3 French), the cross-slit may be located at the inner end of slit 14 in close proximity to tube retaining means 12, whereas if the tube is relatively large (e.g., an outside diameter of 13 millimeters or more), the cross-slit may be located at a substantially greater distance from the retaining means, closer to the opposite end of slit 14. While the provision of a cross-slit facilitates application of the device and helps insure a protective seal between the skin barrier material of the pad and the outer surface of the drainage tube at the point where that tube exits from the patient's body, it is to be understood that at least in some instances the step of forming the cross-slit may be omitted. In any event, the drainage tube should be extended upwardly through the pad at a point along the length of slit 14 that will allow the tube to make a gentle curve or change in direction from vertical to horizontal as depicted in FIG. 3.

With the adhesive pad 11 in place, tube T is laid over plate 20 along the side 21b of wall 21 and tongue 25 is then turned back over the catheter and inserted through opening 21a in the wall. When the free end becomes visible beyond latching tab 30, the user then grips the strap and pulls it into the tube-retaining position depicted in FIGS. 3 and 6. If release of the tube is later required, the user simply lifts the latching member 30 to disengage teeth 31 and 27 and permit the strap to be slid backwardly through opening 21a into its original position.

FIGS. 3 and 6 illustrate the device when used with a relatively small tube or catheter of approximately 2 millimeters outside diameter. The construction of the device, with particular emphasis on the Y-shaped configuration of strap 24, permits tubes of such size, and even substantially smaller, to be securely gripped and retained. In fact, as illustrated in broken lines in FIG. 5, the strap may be advanced so that its loop is closed down to nearly zero diameter. The Y-shaped configuration of the strap, and particularly the spaced arm portions 26 in combination with transverse wall 21, also insure that forces tending to pivot the tube (clockwise or counterclockwise when viewed in FIG. 6) will be effectively resisted.

In the embodiment of FIGS. 1-7, latching member 30 is provided with lateral enlargements or extensions to facilitate gripping and raising the latching member when release of strap 24 is desired. Only slight upward flexing movement of the latching member is required in order to disengage teeth 31 of the member from the teeth 27 of strap 24.

In the embodiment of FIGS. 8-11, the flexible barrier pad 11 may be identical to the pad already described. The difference relate only to tube retaining means 12'. Like tube retainer 12, retainer 12' has a generally planar plate 20' of generally elliptical outline with a transverse wall 21' projecting upwardly from the top surface of the plate. The upstanding wall is parallel with slit 14 and slightly offset from the vertical plane of that slit. Opening 21a' extends through the wall in a direction normal to the vertical plane of the slit and a horizontal recess 22' extends from one side of the wall immediately adjacent opening 21a' to the outer peripheral edge of the plate. The flexible strap 24' is similar to the strap 24 already described except that tongue portion 25' has a pair of spaced, parallel guide ribs 50 extending along its normally upwardly-facing surface. Like strap 24, strap 24' is generally Y-shaped in configuration and includes a pair of diverging arm positions 26' which have their proximal ends joined to wall 21' at points lateral to openings 21a'. Tongue 25' is of substantially uniform width throughout its full length, such width being slightly less than that of opening 21a', and the free end of the tongue (not shown) may be rounded or tapered in the same manner as that of tongue 25. The underside of tongue 25' is provided with a longitudinal series of transversely extending teeth 27'.

In contrast to latching member 30 which has lateral projections or ears 30a to facilitate unlatching of strap 24, the latching member 30' of tube retainer 12' is provided with a longitudinal extension or handle having a narrow stem portion 52 and an enlarged circular end portion 53. Also, retainer 12' includes an integral shell or housing 54 with longitudinal side walls 55 and connecting top wall 56. The top wall is spaced above latching member 30' when that member is in an unflexed or undeformed state (FIGS. 8,9). It serves as a stop to limit the extent of upward flexing action of the latching member when the handle is pulled upwardly in the manner depicted in FIG. 10. It will also be observed that the upper surface of top wall 56 provides a convenient finger-supporting surface when strap 24' is to be released. For example, as depicted in FIG. 10, the enlarged end portion 53 of flexible handle extension 51 may be conveniently gripped between the thumb 57 and index finger 58 and, with the tip of the index finger resting on the upper surface of top wall 56, the hand may be rotated in the direction indicated by arrow 59 to draw the end of latching member 30' upwardly out of engagement with the teeth 27' of strap 24'. The top wall 56 of the shell or housing therefore functions as a fulcrum during a strap-unlatching operation.

As in the first embodiment, plate 20' is provided with a pair of spaced parallel shoulders 32' (FIG. 11) for guiding movement of the strap 24' and insuring proper positioning of the strap beneath latching member 30'. In addition, the plate is provided along its upper surface with a pair of parallel grooves 60 located between and adjacent to shoulders 32' (FIGS. 11, 8). The grooves slidably receive ribs 30 and to that extent may contribute in guiding the strap through open 21a'; however, the primary purpose of the sharp-edged ribs is to secure tube T against longitudinal sliding movement when gripped by the strap and, since such ribs occur only along that portion of the length of the strap provided (on its opposite surface) with teeth 27', grooves 60 function to accommodate the ribs 50 as they pass through the space or opening of latching member 30'. The grooves therefore serve to accommodate the increased thickness of that portion of the strap resulting from the provision of ribs 50.

It will be observed from FIG. 11 that the ribs 50 are tapered or triangular in shape. Their exposed longitudinal edges cause slight deformations in the outer surface of a catheter tube T when strap 24' is tightened, in effect "biting" into the deformable outer surface of the tube to prevent longitudinal displacement of that tube relative to its own axis, or transverse displacement of such tube in relation to the vertical plane of the looped strap 24'.

While in the foregoing, I have disclosed embodiments of the invention in considerable detail for purposes of illustration, it will be understood by those skilled in the art that many of these details may be varied without departing from the spirit and scope of the invention.

I claim:

1. A drainage tube retention device comprising a flexible pad having upper and lower surfaces and having a pressure-sensitive adhesive layer along its lower surface for adherence of the pad to a patient's skin; and tube retaining means upon said upper surface comprising a flexible mounting plate having a bottom surface secured to the upper surface of said pad and having a top surface with a transverse wall projecting upwardly from said top surface, said wall having an opening therethrough extending in a direction parallel with said top surface, a recess in said plate extending from one side of said wall immediately adjacent said opening to the outer periphery of said plate, a flexible strap formed integrally with said plate and extending outwardly from said wall through said recess and beyond said outer periphery of said plate, said strap being Y-shaped in configuration and including an elongated central tongue and a pair of laterally-spaced arms having distal ends merging with said tongue and having proximal ends joined to said plate at points lateral to said opening in said wall, said tongue having a free end portion and being of uniform width throughout substantially its full length, and releasable latching means for latching said strap when the same is reversely turned and the free end thereof is inserted through said opening in said wall from the direction of said arms.

2. The device of claim 1 in which said arms diverge in a proximal direction towards said wall to define, along with said wall, a generally triangular space between said arms.

3. The device of claim 1 in which said opening has a width slightly greater than the width of said tongue.

4. The device of claim 1 in which said opening is of greater width than height.

5. The device of claim 1 in which said plate is imperforate beneath said latching means.

6. The device of claim 1 in which said latching means includes a latching member projecting from said wall in a direction opposite from said strap; said tongue having an undersurface with a longitudinal series of transversely-extending teeth; and said latching member having an underside with at least one tooth engagable with the teeth of said tongue when said strap is reversely turned and inserted through said wall opening.

7. The device of claim 6 in which said top surface of said plate beneath said latching member is imperforate and provides a guide surface for movement of said strap.

8. The device of claim 7 in which a pair of spaced, parallel, guide shoulders project upwardly from said top surface of said plate beneath said latching member for guiding movement of said tongue.

9. The device of claim 6 in which said latching member has a pair of laterally-projecting ear portions adjacent said tooth to facilitate gripping and flexing said latching member out of engagement with the teeth of said tongue when release of said strap is desired.

10. The device of claim 6 in which said latching member includes a flexible, longitudinally-extending, integral handle portion for urging said latching member out of latching engagement with said strap.

11. The device of claim 10 in which said handle portion includes a narrow stem portion and an enlarged end portion.

12. The device of claim 11 in which said end portion is generally circular in shape.

13. The device of claim 6 in which said tube retaining means includes a housing having side and top walls; said top wall extending over said latching member and spaced thereabove when said latching member is in an unflexed state; said top wall constituting stop means for limiting the extent of upward flexing movement of said latching member.

14. The device of claim 6 in which said strap includes a pair of spaced, parallel ribs extending along the surface of said tongue opposite from said series of transversely extending teeth; said mounting plate having a pair of spaced, parallel grooves beneath said latching member for slidably receiving said ribs.

* * * * *